(12) United States Patent
Spindler

(10) Patent No.: US 11,376,113 B2
(45) Date of Patent: Jul. 5, 2022

(54) GRAFT MATERIAL AND METHOD OF USE THEREOF

(71) Applicant: COOK MEDICAL TECHNOLOGIES LLC, Bloomington, IN (US)

(72) Inventor: Ralf Spindler, Solsberry, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 515 days.

(21) Appl. No.: 16/541,459

(22) Filed: Aug. 15, 2019

(65) Prior Publication Data

US 2020/0054436 A1 Feb. 20, 2020

Related U.S. Application Data

(60) Provisional application No. 62/764,778, filed on Aug. 16, 2018.

(51) Int. Cl.
| | |
|---|---|
| *A61F 2/07* | (2013.01) |
| *A61F 2/91* | (2013.01) |
| *A61L 27/52* | (2006.01) |
| *A61L 27/14* | (2006.01) |

(52) U.S. Cl.
CPC ............... *A61F 2/07* (2013.01); *A61F 2/91* (2013.01); *A61L 27/14* (2013.01); *A61L 27/52* (2013.01); *A61F 2002/077* (2013.01); *A61L 2420/08* (2013.01)

(58) Field of Classification Search
CPC ....... A61L 27/14; A61L 27/52; A61L 2420/08
See application file for complete search history.

(56) References Cited

U.S. PATENT DOCUMENTS

| | | |
|---|---|---|
| 5,948,018 A | 9/1999 | Dereume et al. |
| 6,334,868 B1 | 1/2002 | Ham |
| 6,702,849 B1 | 3/2004 | Dutta et al. |
| 6,800,089 B1 | 10/2004 | Wang |
| 6,911,040 B2 | 6/2005 | Johnson et al. |
| 7,118,592 B1 | 10/2006 | Dang et al. |
| 7,288,112 B2 | 10/2007 | Denardo et al. |
| 7,413,573 B2 | 8/2008 | Hartley et al. |
| 8,721,704 B2 | 5/2014 | Cully et al. |
| 8,883,188 B2 | 11/2014 | Dankers et al. |

(Continued)

FOREIGN PATENT DOCUMENTS

| | | |
|---|---|---|
| CA | 2114891 C | 2/1994 |
| CA | 2340439 C | 8/2008 |

(Continued)

OTHER PUBLICATIONS

S. van der Zwaag (ed.), Self-Healing Materials: An Alternative Approach to 20 Centuries of Materials Science, Springer Series in Materials Science, 2007, pp. 1-68 and 95-138.

(Continued)

*Primary Examiner* — Michael C Miggins
(74) *Attorney, Agent, or Firm* — Crowell & Moring LLP

(57) ABSTRACT

The present disclosure relates to a graft material including a reinforced layer and to implantable medical devices including such a graft material. The invention also relates to methods of using and manufacturing such graft materials and devices. In one embodiment the implantable medical device is a stent graft.

20 Claims, 1 Drawing Sheet

(56) References Cited

U.S. PATENT DOCUMENTS

| | | |
|---|---|---|
| 9,687,591 B2 | 6/2017 | Hauser et al. |
| 2002/0096252 A1 | 7/2002 | Lukic |
| 2005/0131519 A1 | 6/2005 | Hartley |
| 2008/0195193 A1 | 8/2008 | Purdy et al. |
| 2015/0093574 A1 | 4/2015 | Tayi et al. |
| 2015/0173921 A1 | 6/2015 | Lavrijsen et al. |
| 2015/0367028 A1* | 12/2015 | Hauser .................. C07K 5/101 424/93.1 |

FOREIGN PATENT DOCUMENTS

| | | |
|---|---|---|
| WO | WO 97/17039 A1 | 5/1997 |
| WO | WO 02/22024 A2 | 3/2002 |

OTHER PUBLICATIONS

D.Y. Wu et al., Self-healing polymeric materials: A review of recent developments, Prog. Polym. Sci. 33 (2008) 479-522, 44 pages.

J. Wu et al., Tough self-healing elastomers by molecular enforced integration of covalent and reversible networks, Adv Mater. Aug. 11, 2017. Doi: 10.1002/adma.201702616 (Epub ahead of print), 32 pages.

V.K. Thakur et al., Self-healing polymer nanocomposite materials: A Review, http://dx.doi.org/10.1016/j.polymer.2015.04.086, ScienceDirect, Polymer 69 (2015) 369-383.

S.M. Kim et al., Superior Toughness and Fast Self-Healing at Room Temperature Engineered by Transparent Elastomers, Adv. Mater., 2017, 1705145, 8 pages.

Y. Wu et al., Bioinspired supramolecular fibers drawn from a multiphase self-assembled hydrogel, PNAS 114 (31), 8163-8168, 2017, 7 pages.

* cited by examiner

GRAFT MATERIAL AND METHOD OF USE THEREOF

RELATED APPLICATIONS

This application claims the benefit of the filing date under 35 U.S.C. § 119(e) of Provisional U.S. Patent Application Ser. No. 62/764,778, filed Aug. 16, 2018, which is hereby incorporated by reference in its entirety.

TECHNICAL

The present disclosure relates to a graft material including a reinforced layer and to implantable medical devices including such a material. The invention also relates to methods of using and manufacturing such graft materials and devices. In one embodiment the device is a stent graft for placement is a vessel of the vascular system for treatment of coronary or peripheral artery disease in a patient.

BACKGROUND

Implantable medical devices, particularly endoluminally deployable medical devices, are known for a variety of medical applications, including the treatment of aneurysms. Aneurysms occur in blood vessels at sites where, due to age, disease or genetic predisposition, the strength or resilience of the vessel wall is insufficient to prevent ballooning or stretching of the wall as blood flows therethrough. If the aneurysm is left untreated, the blood vessel wall may expand to a point at which rupture occurs, often leading to death.

To prevent rupturing of an aneurysm, such as an abdominal aortic aneurysm, a stent graft may be introduced into a blood vessel percutaneously and deployed to span the aneurysmal sac. The outer surface of each end of the stent graft is preferably sealed against the interior wall of the blood vessel at a site where the interior wall has not suffered a loss of strength or resilience. Blood flowing through the vessel is channeled through the hollow interior of the stent graft to reduce, if not eliminate, the stress on the vessel wall at the location of the aneurysmal sac. Therefore, the risk of rupture of the blood vessel wall at the aneurysmal location is significantly reduced or eliminated, and blood can pass through the vessel without interruption.

Stent grafts include a graft fabric secured to a stent. The graft is typically inserted into or pulled over the stent and attached to its structural components. Alternatively, the stent may be formed on the graft such that the individual wires of the stent are threaded through specially provided projecting fabric loops on the surface of the graft. The stent provides rigidity and structure to hold the graft open in a tubular configuration as well as the outward radial force needed to create a seal between the graft and the vessel wall. The graft provides the tubular channel for blood flow past the aneurysm and prevents blood from pressurizing the aneurysmal sac.

However, current stent-graft materials are known to sometimes exhibit a lack of strength. This may have life-threatening consequences when devices incorporating such graft material rupture after being implanted.

SUMMARY

One aspect of the present invention provides a stent graft including an expandable stent and a graft disposed on at least one of the luminal and the abluminal surface of the expandable stent. The graft includes a first layer containing fibers of a supramolecular polymer-colloidal hydrogel. In some embodiments, the graft also includes a second layer disposed on the first layer and including electro-spun polytetrafluoroethylene or expanded polytetrafluoroethylene. In other embodiments, the graft also includes a third layer including electro-spun polytetrafluoroethylene or expanded polytetrafluoroethylene, where the first layer is disposed between the second layer and the third layer.

In some embodiments, the fibers of the supramolecular polymer-colloidal hydrogel are woven, knitted or braided. In other embodiments, the fibers are imbedded in a polymer material, such as polyurethane.

In some embodiments, the supramolecular polymer-colloidal hydrogel includes methyl viologen-functionalized polymer-grafted silica nanoparticles, a semicrystalline polymer in the form of a hydroxyethyl cellulose derivative and cucurbit[8]uril, where the semicrystalline polymer and the methyl viologen-functionalized polymer-grafted silica nanoparticles are cross-linked by the cucurbit[8]uril. The hydroxyethyl cellulose derivative may be naphthalene isocyanate functionalized hydroxyethylcellulose.

In other embodiments the expandable stent comprises a plurality of interconnected struts at least partially imbedded within the first layer. The struts may include nylon, a nickel-titanium alloy, stainless steel or a cobalt-chromium alloy.

In some embodiments, the graft includes a plurality of stacked layers including fibers of the supramolecular polymer-colloidal hydrogel where at least one of the plurality is separated from another of the plurality by a layer comprising electro-spun polytetrafluoroethylene or expanded polytetrafluoroethylene.

The graft may be disposed on the abluminal or the luminal surface of the stent and may attach to the stent by an adhesive or a suture.

Another aspect of the invention provides a graft material including a layer containing fibers of the supramolecular polymer-colloidal hydrogel. The graft may also include a second layer including electro-spun polytetrafluoroethylene or expanded polytetrafluoroethylene, where the second layer is disposed on the first layer. In some embodiments, the graft material also includes a third layer including electro-spun polytetrafluoroethylene or expanded polytetrafluoroethylene, where the first layer is disposed between the second layer and the third layer.

The fibers of the supramolecular polymer-colloidal hydrogel may be woven, knitted or braided. In some embodiments, the fibers are imbedded in a polyurethane. In one embodiment, the supramolecular polymer-colloidal hydrogel includes methyl viologen-functionalized polymer-grafted silica nanoparticles, a semicrystalline polymer in the form of a hydroxyethyl cellulose derivative and cucurbit[8]uril, where the semicrystalline polymer and the methyl viologen-functionalized polymer-grafted silica nanoparticles are cross-linked by the cucurbit[8]uril. The hydroxyethyl cellulose derivative may be naphthalene isocyanate functionalized hydroxyethylcellulose.

In one embodiment, the stent graft includes an expandable stent including a tubular body with a lumen extending therethrough and having a luminal and an abluminal surface. A graft is disposed on at least one of the luminal and the abluminal surface of the tubular body. The graft includes a first layer including fibers of a supramolecular polymer-colloidal hydrogel, a second layer including electro-spun polytetrafluoroethylene or expanded polytetrafluoroethylene, and a third layer including electro-spun polytetrafluoroethylene or expanded polytetrafluoroethylene. The first layer is disposed between the second layer and the third layer.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Figure 1:
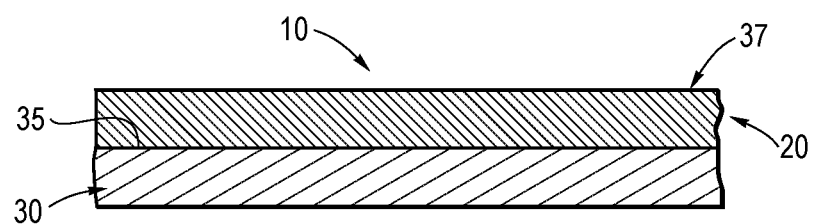
FIG. 1 is a schematic illustration showing one embodiment of a graft of the present invention.

It is to be understood that the drawings are schematic only and not to scale. Often only the principal components relevant to the teachings herein are shown in the drawings, for the sake of clarity.

The term "implantable medical device" refers to a medical device that is either permanently or temporarily inserted into a patient's body for treatment of a medical condition.

The term "luminal surface," as used herein, refers to the portion of the surface area of a medical device defining at least a portion of an interior lumen. Conversely, the term "abluminal surface," refers to portions of the surface area of a medical device defining at least a portion of an exterior surface of the device. For example, where the medical device is a stent-graft having a stent portion with a cylindrical frame formed from a plurality of interconnected struts and bends defining a cylindrical lumen, the abluminal surface can include the exterior surface of the stent, or grant, i.e. those portions of the stent or graft that are placed adjacent or in contact with the vessel wall when the stent-graft is expanded, while the luminal surface can include the interior surface of the struts and bends or covering, i.e. those portions of the device that are placed adjacent or in contact with the vessel interior when the stent-graft is expanded.

The term "therapeutic effect" as used herein means an effect which induces, ameliorates or otherwise causes an improvement in the pathological symptoms, disease progression or physiological conditions associated with or resistance to succumbing to a disorder, for example restenosis, of a human or veterinary patient. The term "therapeutically effective amount" as used with respect to a therapeutic agent means an amount of the therapeutic agent which imparts a therapeutic effect to the human or veterinary patient.

Reinforced Graft Material and Implantable Devices Incorporating such a Graft Material Aspects of the present invention provide reinforced graft materials and implantable medical devices incorporating a graft at least partly formed from such reinforced materials. In certain embodiments, the graft is in the form of a single layer sheet including the reinforced graft material layer, and optionally other materials (reinforced graft material layer}. In other embodiments, the graft is a multilayered sheet including a layer at least partly formed from the reinforced graft material and at least one other layer, the other layer(s) not including the reinforced graft material.

The reinforced graft material layer preferably includes fibers of a supramolecular polymer-colloidal hydrogel. In one embodiment, the supramolecular polymer-colloidal hydrogel includes methyl viologen-functionalized polymer-grafted silica nanoparticles, a semicrystalline polymer in the form of a hydroxyethyl cellulose derivative and cucurbit[8] uril, wherein the semicrystalline polymer and the methyl viologen-functionalized polymer-grafted silica nanoparticles are cross-linked by the cucurbit[8]uril. The hydroxyethyl cellulose derivative may be, for example, naphthalene isocyanate functionalized hydroxyethylcellulose. Such hydrogels may be drawn into supermolecular fibers of arbitrary length using the method of Yuchao Wu et al., "Bioinspired supermolecular fibers drawn from a multiphase self-assembled hydrogel", PHAS, vol. 114, no. 31, pp. 8163-68 (2017).

The layer(s) incorporating the reinforced graft material layers and the other layers may be attached by, for example, pressing the two of more layers together at an elevated temperature. In such a procedure, the temperature should be such that at least one of the layers undergoes at least a limited melting, resulting in a bonding of the layers. In other embodiments, the layers are attached by an adhesive.

In some embodiments, the fibers of the supramolecular polymer-colloidal hydrogel are formed into strands containing multiple fibers. In other embodiments, the fibers, or strands of the fibers, are incorporated into a fabric, for example a knitted, woven or mesh textile material. In yet other embodiments, fibers or strands including the supramolecular polymer-colloidal hydrogel are present between strands of a knitted, woven or mesh textile material formed from another polymeric material.

In one embodiment, each strand is at least partly formed from supramolecular polymer-colloidal hydrogel. For example, an individual strand may be formed from fibers of the supramolecular polymer-colloidal hydrogel without the presence of another material. In other embodiments, each individual strand is formed from a combination of fibers of the supramolecular polymer-colloidal hydrogel and fibers of another natural or synthetic material, such as those disclosed herein.

Each strand may be formed of at least two, three, four, five, six or more fibers aligned with or without a twist. For example, a strand may be formed of one or more fibers of the supramolecular polymer-colloidal hydrogel combined with one or more fibers formed from another material.

In one embodiment, the supramolecular polymer-colloidal hydrogel is continuously integrated along the strand of the material. In yet another embodiment, the supramolecular polymer-colloidal hydrogel is discontinuously integrated along the strand in combination with filaments of other materials.

In some embodiments, the fibers or strands including the supramolecular polymer-colloidal hydrogel are deposited to form a matrix at least partially embedded between strands of a woven, knitted or mesh material formed from a natural or synthetic textile material. Example of such synthetic materials include, for example, polyesters, such as poly(ethylene terephthalate); fluorinated polymers, such as polytetrafluoroethylene (PTFE) and fibers of expanded PTFE; polyethylene, polypropylene, polyaramids, polyacrylonitrile, nylons and polyurethanes. In addition, materials that are not inherently biocompatible may be suitable for use as textile strands if they can be rendered biocompatible. For example, surface modification techniques may be employed to impart biocompatibility to such materials. Examples of surface modification techniques include graft polymerization of biocompatible polymers from the material surface, coating of the surface with a crosslinked biocompatible polymer, chemical modification with biocompatible functional groups, and immobilization of a compatibilizing agent such as heparin or other substances.

In certain embodiments, the graft may include multiple reinforced graft material layers and/or other layers. For example, a reinforced graft material layer may be positioned between two other layers to form a multilayered graft. More complex grafts may be formed, including grafts with multiple altering reinforced graft material layers and other layers. For example, the graft may include 2, 3, 4, 5, 6, 7, 8, 9, 10 or more reinforced graft material layers. In such embodiments, each reinforced graft material layer is separated from and attached to another reinforced graft material layer by an intervening layer not including the reinforced graft material. In other embodiments, the graft may include two, three, four, five or more layers including the reinforced graft material attached directly to each other. In such embodiments, these layers may include additional materials as disclosed herein, with the same or different additional material being included in each layer.

The other layers present in the graft may be porous layers and, in certain embodiments, one of these layers forms the outermost layer of the graft. For example, when the graft is utilized as the graft of a vascular stent-graft device, this outermost layer may form the abluminal surface of the device and be placed in contact with the blood vessel wall when the stent-graft device is implanted in the body of a patient. In such embodiments, the porous layer allows for cellular migration when the device is implanted.

In some embodiments, the other layers of the graft are formed from a polymeric material such as polyethylene, polypropylene, polyaramids, polyacrylonitrile, nylons, cellulose, polyester, a fluorinated polymer or polyurethane, or combinations of these materials. In certain embodiments, the other layer(s) include at least one of electrospun polytetrafluoroethylene "(esPTFE)" and expanded polytetrafluoroethylene ("ePTFE"). Preferably, the layer is formed from only one of these materials. esPTFE is formed by the use of an electric force to draw charged threads of PTFE polymer solutions or polymer melts up to fiber diameters in the order of some hundred nanometers.

ePTFE has a micro-structure characterized by nodes interconnected by fibrils of the polymer. The material is formed by expanding paste-formed products of a tetrafluoroethylene polymer to form a material having high porosity and high strength. The fibrils of the polymer are substantially orientated in the direction of the expansion of the material. Both esPTFE and ePTFE materials are commercially available in sheet form from, for example, Zeus Industrial Products, Inc., Orangeburg, S.C. 29115.

In those embodiments where the graft includes multiple layers of ePTFE, the orientation of the individual layers of ePTFE within the graft may vary with respect to the direction of expansion (and fibril orientation) of the ePTFE. For example, some embodiments may include an ePTFE layer positioned with the direction of expansion parallel to an axis of the device and another ePTFE layer positioned with the direction of expansion positioned at an angle, for example perpendicular to, that axis.

In other embodiments, the graft may include a "mat" layer that provides for additional load bearing capacity to the graft. In such embodiments, the mat layer may be attached to the reinforced graft material layer and/or to a layer not including the reinforced graft material. The graft may include 1, 2, 3, 4, or more mat layers. In some embodiments, the mat layer is a mesh or a braided, woven or knitted layer. The mat layer may be formed from, for example, polyether ether ketone (PEEK), Polyethylene terephthalate (PETE), ultra-high-molecular-weight polyethylene (UHMWPE), nylon, or a metallic material, such as a super-elastic nickel-titanium alloy (e.g. NITINOL), stainless steel, gold, platinum, palladium, titanium, tantalum, tungsten, molybdenum, cobalt-chromium alloy, such as L-605, MP35N, Elgiloy; nickel-chromium alloys, such as alloy 625; and niobium alloys, such as Nb-1% Zr.

The graft may form part of implantable medical devices such as, but not limited to, endovascular grafts, vascular grafts, stent grafts, balloon catheters, meshes, filters (e.g., vena cava filters), tissue scaffolds, myocardial plugs, valves (e.g., venous valves), pelvic implants, various types of dressings, or other known implantable devices, including flat sheet structures such as hernia patches, skin graft patches, bone stabilization devices or bandages.

The medical device may be a bifurcated integrated stent-graft, an integrated stent-graft configured for any blood vessel including coronary arteries and peripheral arteries (e.g., renal, superficial femoral, carotid, and the like), a urethral integrated stent-graft, a biliary integrated stent-graft, a tracheal integrated stent-graft, a gastrointestinal integrated stent-graft, or an esophageal integrated stent-graft, for example.

Typically, in stent-graft devices, the graft is attached to the stent portion of the devices by, for example, sutures or an adhesive, so that when the stent is expanded alter delivery to the treatment site, the fabric material contacts the vessel wall and provides support for any weakness present.

In preferred embodiments, a graft as described herein is attached to a balloon expandable or self-expanding stent to form a stent-graft device. The stent portion of the device is generally formed of at least one tubular portion and may be configured as a unitary structure or as a plurality of attached portions, for example, attached tubular portions or a plurality of interconnected struts, which may collectively define the stent portion. The tubular portion may be made from a woven or knitted structure, a laser-cut cannula, individual interconnected rings, or another pattern or design.

The stent portion may be formed from a metallic material such as stainless steel, super-elastic nickel-titanium (NITINOL), silver, platinum, palladium, gold, titanium, tantalum, iridium, tungsten, cobalt, chromium, cobalt-chromium alloy, cobalt-based alloy, nickel-based alloy or molybdenum alloy. Biodegradable metals may also be used, including, for example, a biodegradable magnesium alloy.

In other embodiments, the stent portion may by formed from a biodegradable or non-biodegradable polymeric material. Nonbiodegradable polymers that can be used include for example cellulose acetate, cellulose nitrate, silicone, polyethylene terephthalate, polyurethane, polyamide, polyester (e.g. Nylon), polyorthoester, polyanhydride, polyether sulfone, polycarbonate, polypropylene, high molecular weight polyethylene, and polytetrafluoroethylene, or mixtures of these materials. Biodegradable polymers that can be used include for instance polylactic acid (PLA), polyglycolic acid (PGA), poly(lactic-co-glycolic acid) (PLGA), polyanhydride, polycaprolactone, polyhydroxybutyrate valerate, or mixtures of these materials.

The graft may be attached to the stent portion of the device by, for example, adhesive, sutures, staples or clips. Alternatively, or as well as, the stent portion of the stent-graft may be at least partially imbedded into one of the reinforced graft material layers of the graft. In other embodiments, the stent portion of the stent-graft is at least partially imbedded into one of the layers not including the reinforced graft material.

In some embodiments, the reinforced graft material is present throughout the graft portion of the device. In other embodiments, the reinforced graft material is present only, or is present in an higher amount, at those portions of the graft that attach to an associated stent device. For example, in devices such as a bifurcated integrated stent-graft used to treat abdominal aortic or aorto-iliac aneurysms, the graft may be additionally reinforced in the region of the aorta and/or the renal regions where the graft attaches to the expandable portion of the device, by, for example, sutures.

Non limiting examples of grafts as disclosed herein and stent-graft devices incorporating such grafts will now be illustrated with reference to FIGS. 1 to 9. Referring first to the FIG. 1, which is a schematic illustration of a cross-sectional view of one embodiment of a graft of the present invention. In this embodiment, graft 10 is a two-layered structure including a reinforced graft material layer 20 having a first surface 35 attached to a second layer 30. In this embodiment, second layer 30 does not include the reinforced graft material. In another embodiment, the graft includes a third layer (not illustrated) attached to second surface 37 of reinforced graft material layer 20. In some embodiments, the second and/or third layers are formed from either esPTFE or ePTFE polymer.

Figure 2:
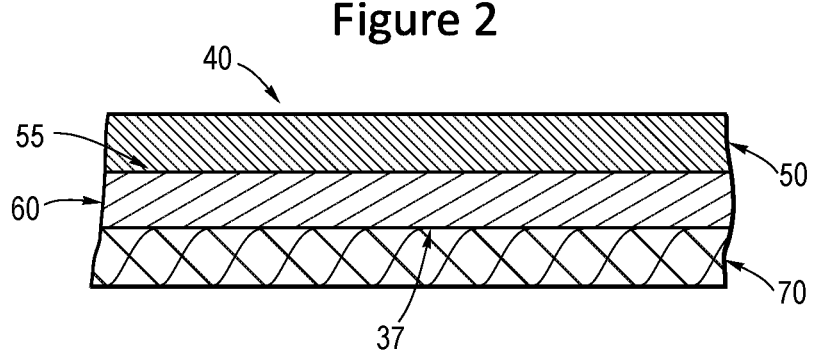
FIG. 2 is a schematic illustration showing another embodiment of a graft of the present invention.

FIG. 2 is a schematic illustration showing a cross-sectional view of another embodiment of a graft. In this embodiment, graft 40 is a three-layered structure including layer 50 bonded to a first surface 55 of reinforced graft material layer 60. Layer 50 may be formed from, for example, esPTFE or ePTFE polymer. Layer 70 attaches to a second surface 37 of reinforced graft material layer 60 and may include a "mat" layer as disclosed herein.

Figure 3:
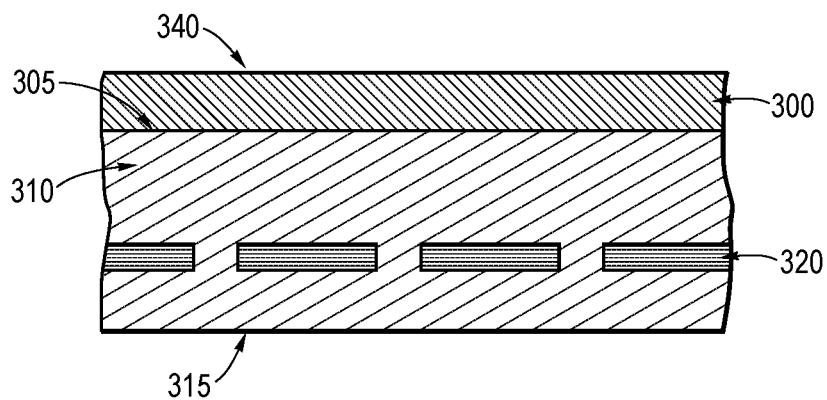
FIG. 3 is a schematic illustration showing an embodiment of part of a stent-graft including one embodiment of a graft of the present invention.

FIG. 3 shows a cross-sectional view of a portion of one embodiment of a stent-graft including a graft as disclosed herein. Stent-graft 340 includes stent portion 320, which in imbedded within layer 310, which may include a reinforced graft material. Layer 300 attaches to surface 305 of 310 and may form the luminal or the abluminal surface of stent-graft device 340. In other embodiments, a third layer (not illustrated) lay be attached to second surface 315 of layer 310.

Implantable Devices Incorporating a Bioactive Agent

The grafts and implantable medical devices disclosed herein may also include a therapeutically effective amount of a bioactive agent. For example, the bioactive agent may be incorporated into the graft and/or into another component of the device. For example, in the case of stent-graft devices, the bioactive agent may be incorporated into the one or more layers of the graft. The bioactive material may be incorporated during the manufacturing process used for form the individual layers of the graft, for example when forming the reinforcement, mat and/or bonding layers. In other embodiments, the bioactive agent may be impregnated into the graft after it has been formed by combining the individual layers.

The bioactive agent may be selected to perform a desired function upon implantation. Bioactive agents within the scope of the present embodiments include antiproliferative agents immunosuppressive agents, restenosis-inhibiting agents, anti-cancer agents, analgesics/antipyretics, anesthetics, antiasthmatics, antibiotics, antidepressants, antidiabetics, antifungal agents, antihypertensive agents, anti-inflammatories, antineoplastics, antianxiety agents, sedatives/hypnotics, antianginal agents, nitrates, antipsychotic agents, antimanic agents, antiarrhythmics, antiarthritic agents, antigout agents, thrombolytic agents, hemorheologic agents, anticonvulsants, antihistamines, agents useful for calcium regulation, antibacterial agents, antiviral agents, antimicrobials, anti-infectives, bronchodilators, steroids and hormones.

Non-limiting examples of such drugs include doxorubicin, cam ptothecin, etoposide, mitoxantrone, cyclosporine, epothilones, napthoquinones, 5 fluorouracil, methotrexate, colchicines, vincristine, vinblastine, gemcitabine, statins (for example atorvastatin, fluvastatin, lovastatin, pitavastatin, pravastatin, rosuvastatin and simvastatin), steroids (for example cortisteroids, prednisilone and dexamethazone) mitomycin and derivatives or analogues of these agents.

Preferred bioactive agents include restenosis-inhibiting agents a, including but not limited to microtubule stabilizing agent such as paclitaxel, a paclitaxel analog, or a paclitaxel derivative or other taxane compound; a macrolide immunosuppressive agent such as sirolimus (rapamycin), pimecrolimus, tacrolimus, everolimus, zotarolimus, novolimus, myolimus, temsirolimus, deforolimus, or biolimus; an antiproliferative agent; a smooth muscle cell inhibitor; an inhibitor of the mammalian target of rapamycin (mTOR inhibitor).

Certain bioactive agents may be present in more than one polymorphic form. For example, paclitaxel may be present as at one of Solid forms of amorphous paclitaxel ("aPTX"), dihydrate crystalline paclitaxel ("dPTX") and anhydrous crystalline paclitaxel.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

What is claimed is:

1. A stent graft comprising:
an expandable stent having a luminal and an abluminal surface; and
a graft disposed on at least one of the luminal and the abluminal surface;
wherein the graft comprises a first layer comprising fibers of a supramolecular polymer-colloidal hydrogel.

2. The stent-graft of claim 1, wherein the fibers of a supramolecular polymer-colloidal hydrogel are woven, knitted or braided.

3. The stent-graft of claim 1, wherein the fibers of a supramolecular polymer-colloidal hydrogel are imbedded in a polyurethane.

4. The stent graft of claim 1, wherein the graft comprises a plurality of stacked layers comprising fibers of the supramolecular polymer-colloidal hydrogel wherein at least one of the plurality of stacked layers is separated from another of the plurality of stacked layers by a layer comprising electro-spun polytetrafluoroethylene or expanded polytetrafluoroethylene.

5. The stent graft of claim 1, wherein the first layer is disposed on the abluminal surface of the stent.

6. The stent graft of claim 1, wherein the first layer attaches to the expandable stent by an adhesive or a suture.

7. The stent graft of claim 1, wherein the graft further comprises a second layer comprising electro-spun polytetrafluoroethylene or expanded polytetrafluoroethylene, wherein the second layer is disposed on the first layer.

8. The stent graft of claim 7, wherein the graft further comprises a third layer comprising electro-spun polytetrafluoroethylene or expanded polytetrafluoroethylene, wherein the first layer is disposed between the second layer and the third layer.

9. The stent graft of claim 1, wherein the supramolecular polymer-colloidal hydrogel comprises methyl viologen-functionalized polymer-grafted silica nanoparticles, a semicrystalline polymer in the form of a hydroxyethyl cellulose derivative and cucurbit[8]uril, wherein the semicrystalline polymer and the methyl viologen-functionalized polymer-grafted silica nanoparticles are cross-linked by the cucurbit[8]uril.

10. The stent graft of claim 9, wherein hydroxyethyl cellulose derivative is naphthalene isocyanate functionalized hydroxyethylcellulose.

11. The stent graft of claim 1, wherein the expandable stent comprises a plurality of interconnected struts at least partially imbedded within the first layer.

12. The stent graft of claim 11, wherein the struts comprise a material selected from the group consisting of nylon, a nickel-titanium alloy, stainless steel and a cobalt-chromium alloy.

13. An expandable stent graft material comprising a first layer comprising fibers of a supramolecular polymer-colloidal hydrogel.

14. The graft material of claim 13, wherein the fibers of a supramolecular polymer-colloidal hydrogel are woven, knitted or braided.

15. The graft material of claim 13, wherein the fibers of a supramolecular polymer-colloidal hydrogel are imbedded in a polyurethane.

16. The graft material of claim 13, further comprising a second layer comprising electro-spun polytetrafluoroethylene or expanded polytetrafluoroethylene, wherein the second layer is disposed on the first layer.

17. The graft material of claim 16, wherein the graft material further comprises a third layer comprising electro-spun polytetrafluoroethylene or expanded polytetrafluoroethylene, wherein the first layer is disposed between the second layer and the third layer.

18. The graft material of claim 13, wherein the supramolecular polymer-colloidal hydrogel comprises methyl viologen-functionalized polymer-grafted silica nanoparticles, a semicrystalline polymer in the form of a hydroxyethyl cellulose derivative and cucurbit[8]uril, wherein the semicrystalline polymer and the methyl viologen-functionalized polymer-grafted silica nanoparticles are cross-linked by the cucurbit[8]uril.

19. The graft material of claim 18, wherein hydroxyethyl cellulose derivative is naphthalene isocyanate functionalized hydroxyethylcellulose.

20. A stent graft comprising:
an expandable stent comprising a tubular body with a lumen extending therethrough and having a luminal and an abluminal surface; and
a graft disposed on at least one of the luminal and the abluminal surface;
wherein the graft comprises:
a first layer comprising fibers of a supramolecular polymer-colloidal hydrogel;
a second layer comprising electro-spun polytetrafluoroethylene or expanded polytetrafluoroethylene; and
a third layer comprising electro-spun polytetrafluoroethylene or expanded polytetrafluoroethylene,
wherein the first layer is disposed between the second layer and the third layer.

* * * * *